United States Patent [19]

King et al.

[11] Patent Number: 5,104,492
[45] Date of Patent: Apr. 14, 1992

[54] RECOVERY OF CARBOXYLIC ACIDS FROM WATER BY PRECIPITATION FROM ORGANIC SOLUTIONS

[75] Inventors: C. Judson King, Kensington; John Starr, Albany, both of Calif.

[73] Assignee: The Regents of the University of California, Oakland, Calif.

[21] Appl. No.: 550,959

[22] Filed: Jul. 11, 1990

[51] Int. Cl.$^5$ .................. B01D 3/00; C07C 51/48
[52] U.S. Cl. .................. 203/15; 203/43; 203/47; 203/48; 562/485; 562/486; 562/490; 562/494; 562/554; 562/593
[58] Field of Search ........ 203/15, 43, 47, 48, 203/16; 562/593, 485, 486, 490, 494, 554, 606

[56] References Cited

U.S. PATENT DOCUMENTS

| | | | |
|---|---|---|---|
| 2,398,485 | 4/1946 | Wilson | 562/593 |
| 2,539,472 | 1/1951 | Ratchford et al. | 562/580 |
| 2,592,964 | 4/1952 | Smith | 562/593 |
| 3,023,238 | 2/1962 | Chapman et al. | 203/48 |
| 3,329,712 | 7/1967 | Danly et al. | 562/593 |
| 3,786,096 | 1/1974 | Konno | 562/593 |
| 3,810,937 | 5/1974 | Kuceski | 562/593 |
| 4,191,616 | 3/1980 | Baker | 203/48 |
| 4,230,887 | 10/1980 | Mitchell et al. | 203/15 |
| 4,275,234 | 6/1981 | Baniel et al. | 562/584 |
| 4,705,894 | 11/1987 | Su et al. | 562/593 |

FOREIGN PATENT DOCUMENTS

| | | | |
|---|---|---|---|
| 52-19618 | 2/1977 | Japan | 562/593 |
| 53-79815 | 7/1978 | Japan | 562/593 |
| 431313 | 7/1935 | United Kingdom | 203/15 |

OTHER PUBLICATIONS

C. J. King, Int. Solvent. Extraction Conf., *Conference Papers*, 1:19-24 (1988).
Forbes, G. S. et al., *J. Am. Chem. Soc.*, 41(2), 150-167 (1919).
Sato, T. et al., *Bunseki Kagaku*, 34, 557-563 (1984).
Lipovskii, A. A. et al., *Radiokhimiya*, 10(2), 175-181 (1968).

*Primary Examiner*—Wilbur Bascomb, Jr.
*Attorney, Agent, or Firm*—Morrison & Foerster

[57] ABSTRACT

Carboxylic acids are recovered from wet organic solutions by reducing the solutions' water content thus causing the acids to precipitate as recoverable crystals.

29 Claims, 2 Drawing Sheets

RECOVERY OF CARBOXYLIC ACIDS FROM WATER BY PRECIPITATION FROM ORGANIC SOLUTIONS

ORIGIN OF THE INVENTION

This invention was made in the performance of a contract granted by the United States Department of Energy. The United States Federal Government may have rights to this invention.

TECHNICAL FIELD

The present invention relates to a process for the recovery of carboxylic acids from organic solutions by precipitation. In one embodiment it relates to the recovery of a carboxylic acid from an aqueous solution by 1) extracting the solution with an appropriate water-saturated nonaqueous solvent, 2) dewatering the extract to reduce the level of water present to a level at which the acid is less soluble and thus to precipitate the carboxylic acid, and 3) recovering the precipitated acid. The process can effect separation of mixtures of acids, as well.

BACKGROUND OF THE INVENTION

Carboxylic acids are important chemicals of commerce. They appear as desired or contaminating constituents of a wide range of aqueous and organic process streams. Historically, they were produced from animal fat or vegetable oil sources or from petroleum sources in substantially nonaqueous systems. More recently they have been identified among the most attractive products for manufacture from biomass (e.g. corn starch) by fermentation. In these more advanced processes, the carboxylic acid is generated as a dilute solution in an aqueous fermentation broth. Acetic acid is recovered commercially from dilute aqueous solutions by extraction with solvents such as isopropyl acetate, other esters, or ethers. Aqueous solutions are created during the manufacture of adipic acid. Citric acid is recovered from fermentation broths commercially by solvent extraction with high-molecular-weight tertiary amines (e.g. tridecylamine) in a diluent composed of a hydrocarbon (e.g. kerosene) and an alcohol (e.g. n-decanol). Citric acid commands a substantial market, which is increasing as detergent manufacturers switch to citric acid as "builder". Lactic acid (raw material for biodegradable plastics), succinic acid, malic acid, fumaric acid, and other carboxylic acids which may be manufactured on a large scale by fermentation of biomass are creating considerable interest in solvent extraction as a means of recovery. Carboxylic acids are also stable oxidation products and frequently appear as by-products or contaminants in aqueous and organic waste streams.

Biomass source streams and the like from which carboxylic acids are to be recovered are typically dilute aqueous solutions. Solvent extraction is one widely studied method for recovering carboxylic acids from such streams. This forms an organic solvented solution of the acids. A cost-effective solvent-extraction process for isolating carboxylic acids requires an efficient method for recovering the acids from the organic phase. A sufficiently volatile carboxylic acid can be recovered from an organic phase by distillation, as is done commercially for acetic acid. However, the dicarboxylic and hydroxycarboxylic acids have very low volatilities and cannot be recovered in this way.

Prior workers have suggested a variety of processes for recovering low-volatility carboxylic acids following extraction. A. Baniel et al., in U.S. Pat. No. 4,275,234, describe recovering citric acid from an organic extract by back-extraction into water following a change (usually an increase) in temperature. Evaporation and crystallization are still required to isolate the product acid. Baniel et al. also suggest back-extraction into water following a change in composition of the organic extract, e.g. by distilling a component out of the extract and recycling that component back to the extraction zone. Evaporation and crystallization of the back extract are again required to isolate the product acid. A similar process was set out by J. Tamada and C.J. King in a paper presented at the International Solvent Extraction Conference, Moscow, USSR, July 1988.

W. P. Ratchford et al., in U.S. Pat. No. 2,539,472, describe the extraction of water-soluble carboxylic acids from fermentation broths. R. D. Chapman et al., in U.S. Pat. No. 3,023,238, describe recovery of a carboxylic acid from an aqueous solution by evaporative crystallization. Solvent extraction of a mixture of carboxylic acids and fractional extraction to isolate the individual acids are described in Danly et al., U.S. Pat. No. 3,329,712. K. Konno, in U.S. Pat. No. 3,786,096, describes solvent extraction of adipic acid from an aqueous solution with cyclohexanone and/or cyclohexanol, but not the recovery of the acid from the extract. V. P. Kuceski, in U.S. Pat. No. 3,810,937, describes schemes for recovering adipic acid from solvent solutions that include evaporation of the solvent, esterification of the acid, and back extraction of the ester into water. Recovery and fractionation of carboxylic acids by codistillation with a suitable alkylbenzene is described by B. Baker, in U.S. Pat. No. 4,191,616.

Three references which concern changes in solubility of carboxylic acids in organic liquids with changes in water content of the organic phase are as follows: Forbes, G.S. and Coolidge, A.S., *J. Am. Chem. Soc.*, 41(2),150-67, (1919) found increasing acid solubility as the water concentration in an organic solvent increased. The system they worked with was succinic acid—diethyl ether—water. They noted the change, but give no indication of applying it to the process which is this invention. Sato, T., Watanabe, H., and Nakamura, H., *Bunseki Kaoaku*, 34,557-63, (1984) reported that in the extraction of lactic acid, succinic acid, and citric acid into a mixed solvent of xylene and trioctylamine, the amount of water in the organic phase decreased with an increase in the acid concentration in the organic phase. Lipovskii, A.A. and Kuzina, M.G., *Radiokhimiya*, 10(2), 175-81, (1968) studied the extraction of oxalic acid into solutions of trioctylamine (TOA) in chloroform and TOA in benzene. The solid TOA-bioxalate salt with $TOA:H_2C_2O_4$ ratios of 2:1 and 1:1 did not dissolve into anhydrous chloroform or anhydrous benzene. Water was added to the organic phase in order to get the salt to dissolve. However, the salt with $TOA:H_2C_2O_4$ ratios of 1:1 and 1:2 did dissolve in anhydrous chloroform.

DISCLOSURE OF THE INVENTION

We now have found an improved process for recovering carboxylic acids from organic solutions thereof.

This process is based on our discovery that the solubility of carboxylic acids in organic solvents is heavily directly dependent upon the water content of the solvent.

In its broadest aspects, the invention provides a process for recovering carboxylic acids from water-wet organic solutions by dewatering the solution, thereby creating an organic solution in which the carboxylic acid is less soluble and from which it precipitates and is recovered.

In some embodiments, the dewatering is carried out by stripping, in others adsorption, absorption or membrane processes are used.

The process can be used on acid-containing organic streams irrespective of source but can find good application to remove acids from organic extracts produced in organic/aqueous solvent extractions.

In one aspect of the embodiment, the invention provides a process for recovering a carboxylic acid from an aqueous starting solution. In this process the aqueous solution is first contacted with a substantially water-immiscible but water-wettable organic solvent. Two phases are formed, one a carboxylic acid-depleted aqueous raffinate and the other a carboxylic acid enriched water-wet solvent extract. The phases are then separated and the carboxylic acid-enriched water-wet solvent extract is dewatered. This dewatering markedly decreases the solubility of the acid in the extract solvent and generates a carboxylic acid containing bottoms product from which the carboxylic acid can be directly recovered as a precipitate. ("Water-wettable" means that the solvent will take up to about 20% by weight of water in a water-solvent two component mixture.)

In another aspect, the invention can serve to separate two or more carboxylic acids of differing solubilities.

DETAILED DESCRIPTION OF THE INVENTION

This invention achieves the recovery of carboxylic acids from organic solutions by extracting the acid into an organic solvent (optionally formed by solvent extracting an aqueous phase). The organic solution is dewatered. This causes precipitation of the carboxylic acid in the remaining organic solvent. The solid carboxylic acid product is then separated from the liquid solvent.

The removal of the water has an unexpectedly marked effect on the acid's solubility in the organic solvent and leads to the acid's substantial precipitation. This allows isolation of the acid without the removal of a large fraction of the organic solvent as might be expected in a normal crystallization. Energy consumption is therefore low. Additionally, because the removed solvent and the precipitation mother liquor can be recycled, there is a major reduction of waste products generated in the processing.

In this Detailed Description section, first, the process will be described step by step and then the types of acids recoverable and representative feed stocks will be described. Next, the selection criteria and spectrum of appropriate organic solvents will be set forth. Several Examples are then provided.

The Process

Figure 1:
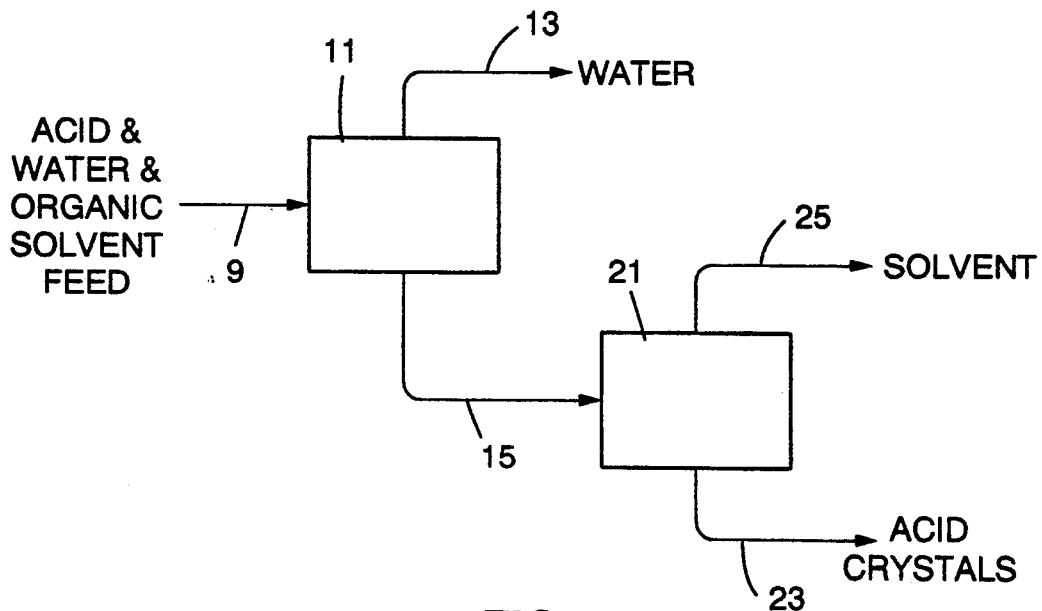
FIG. 1 is a schematic flow diagram depicting one embodiment of this process.

In FIG. 1, a very simple and general embodiment of the invention is shown. A feed stream of carboxylic acid dissolved in a water-wet organic solvent is passed through line 9 to water removal zone 11. Water removal zone 11 can be an evaporative dewaterer such as a stripper, a distillation column or an evaporative crystallizer. It can also be a reverse osmosis or dialysis device which employs a semipermeable membrane to selectively pass water molecules while retaining the solvent and acid molecules. It can also be an absorption or adsorption zone where the feed is contacted with a material such as 3A molecular sieves, porous silica gel or the like which is capable of preferentially taking up water from the feed. By any of these methodologies water is removed in zone 11 and taken off via line 13. The amount of water taken off can vary. Generally, to achieve an efficient acid recovery, the water level should be reduced at least to the lower of 5% by weight or ½ the water content of the feed stream. Preferably the water level is reduced to the lower of below 1% by weight or ¼ the water content of the feed stream.

The dewatered organic solvent/carboxylic acid mixture is taken off via line 15. The dewatering causes the acid to precipitate, either in zone 11 or, if called for by the nature of the dewatering process, in a separate chiller or the like not shown in FIG. 1. The solid acid/liquid solvent mixture is separated in separation zone 21. Zone 21 can be a centrifuge, a filter, a settling/decantation basin or any other unit which will permit a liquid solvent phase to be separated and removed via line 25 and a solid acid phase to be separated and removed via line 23.

Figure 2:
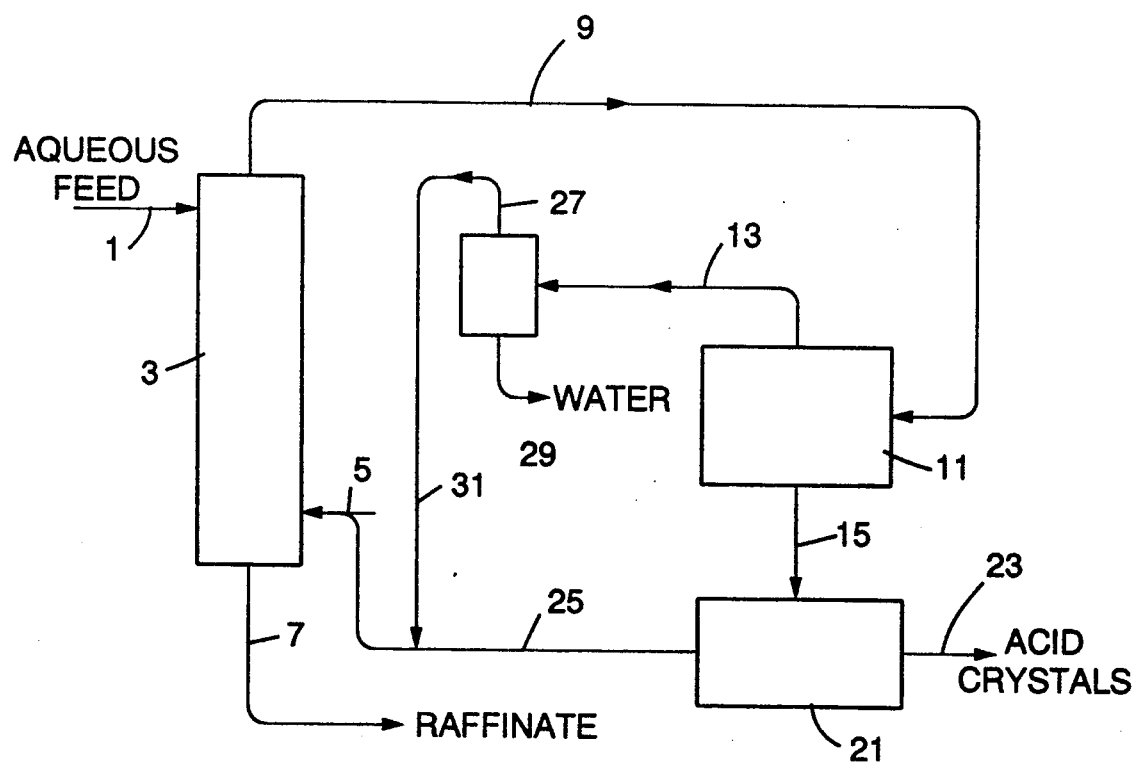
FIG. 2 is a schematic flow diagram depicting a second embodiment of this invention.
Figure 3:
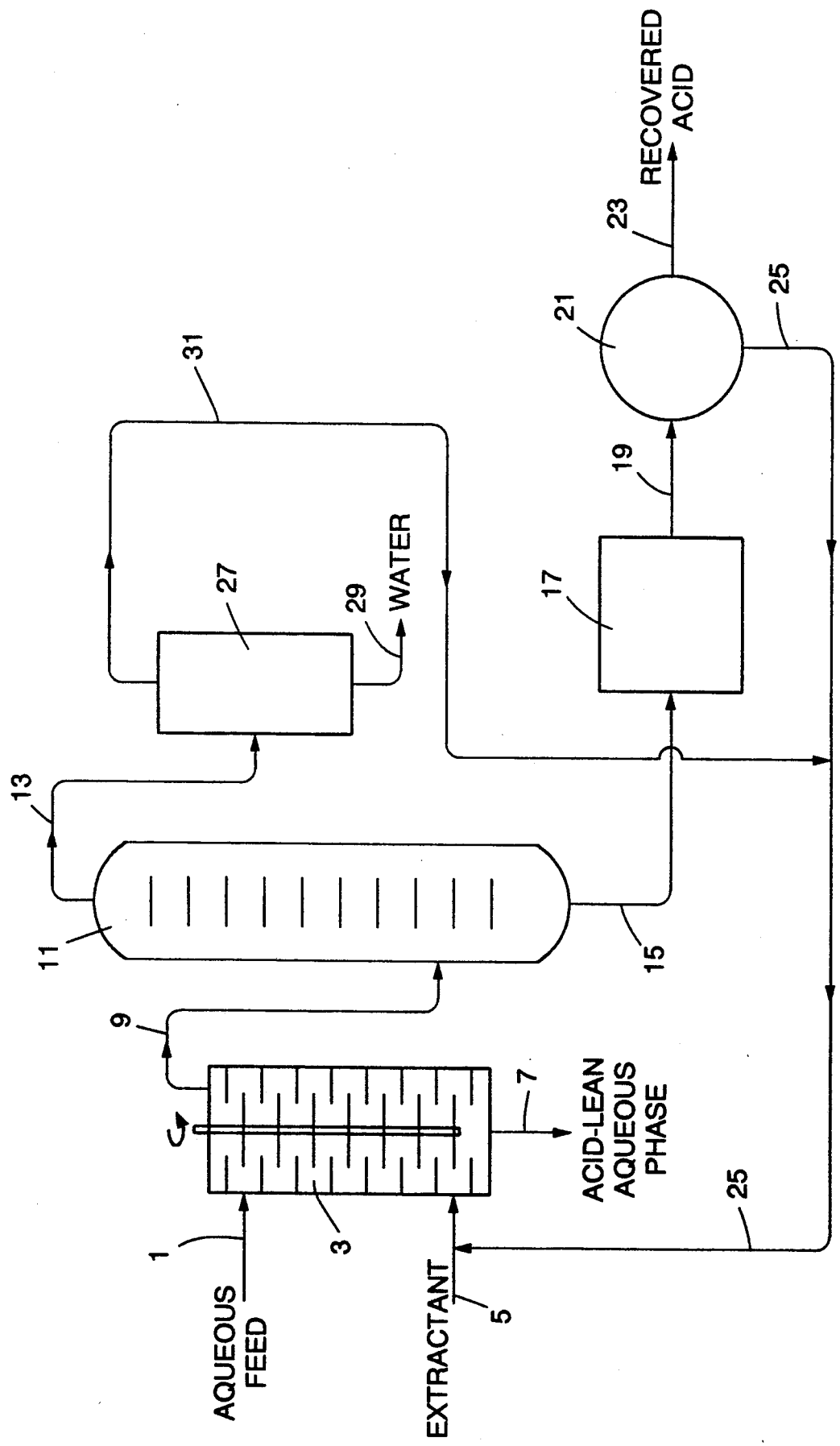
FIG. 3 is a schematic flow diagram depicting a third embodiment of this invention.

FIGS. 2 and 3 depict two further embodiments of the invention. In these embodiments additional steps are employed to allow the process to work on the recovery of acids which are being solvent extracted into an organic phase from a starting aqueous phase.

In both cases, an aqueous starting solution containing about 3% by weight of adipic acid is fed through line 1 to extraction vessel 3 where it is contacted with cyclohexanone fed through line 5. Vessel 3 is shown in FIG. 3 as a countercurrent rotating disc contactor in which the lighter ketone phase moves upward through the descending aqueous phase. Other equivalent contactors such as mixer followed by a phase separator can be used as well.

The volume ratio of aqueous feed to ketone is about 1:0.5.

This contacting causes the adipic acid present in the aqueous phase to partition preferentially into the ketone phase. It also causes the ketone to become saturated with water (up to about 16% by weight $H_2O$ depending upon the amount of acid taken up, as well). The acid-lean aqueous raffinate is taken off through line 7 either to waste or to subsequent processing to recover dissolved or entrained extractant ketone or other recoverable components. The water-saturated acid-rich extract is taken off through line 9 to dewatering zone 11. Dewatering zone 11 can be a single stage or multistage as shown. In FIG. 2, the dewatering zone is an evaporative crystallizer in which heat (and optionally reduced pressure) strip water and some of the solvent overhead. In FIG. 3, the zone 11 is shown as a distillation column. In dewatering zone 11, an overhead fraction made up of water and cyclohexanone (and any similarly volatile materials extracted from the aqueous feed) is taken off through line 13. This overhead is typically 3 to 60% of the volume fed to the dewatering zone. A bottom product which is substantially reduced in water level (typically to less than 1% by weight) and which also contains the adipic acid is taken off through line 15.

In the case shown in FIG. 2, the bottom product in line 15 contains solid adipic acid as a slurry in cyclohexanone. This slurry is separated in centrifuge 21 to give solid acid taken off through line 23 and cyclohexanone which is taken off through line 25 to line 5.

In the case shown in FIG. 3, the dewatered product of zone 11 is a solution. Line 15 conveys this solution to precipitator 17 where it is chilled to form an adipic acid slurry which is passed through line 19 to solid/liquid separator 21 (e.g., filter, centrifuge, or the like), where precipitated adipic acid is recovered as a solid and taken off via line 23. The ketone mother liquor of the precipitation is removed via line 25 for recycle to the extraction vessel 3 as shown.

The water and ketone stripped overhead and taken off via line 13 is preferably recycled as well. This stream can be condensed and phase separated in condensor 27 to remove water and other impurities via line 29 and generate ketone for recycle via line 31 and line 25.

This process can be practiced in a batch mode, as well, if desired.

The Acids Recovered

The acids recovered by this process are carboxylic acids which exist as solids at temperatures of $-25°$ C. or higher so as to be recovered as solid precipitates in accord with this invention. In those cases where water is removed by evaporation, the acid must be nonvolatile. (An acid is considered nonvolatile if its atmospheric boiling point is above $125°$ C.) These acids include aliphatic polycarboxylic acids and aromatic mono- and polycarboxylic acids. The aliphatic polycarboxylic acids include di-, tri- and higher carboxyl materials particularly the 2-12 even carbon number diacids (i.e., diacids of 2, 4, 6, 8, 10 or 12 carbon atoms) such as oxalic acid, succinic acid, sebacic acid, adipic acid, and fumaric acid. The aromatic acids include aromatic monoacids of 7 to 13 carbon atoms such as benzoic acid, cinnamic acid, phenylacetic acid, naphthoic acid, and the like and diacids of 8 to 12 carbons such as phthalic acid. In addition to these simple oxyhydrocarbon acids, the process can be used to recover those more complex materials, such as amino acids and the like which exhibit the same organic solubility variation with water content. Other functional groups such has halogens or nitro groups may be present on the acid solute.

When these acids are present in and extracted from water-based feedstocks, the feedstocks will contain from about 10 ppm to saturation (for example, up to about 30% by weight) of acids. The feedstocks can contain a mixture of these acids and the present process can fractionate this mixture if solubilities permit. The feedstock can contain other materials such as salts and organics (sugars, starches, alcohols, aldehydes and the like).

The Solvent

The organic solvent from which the acids are precipitated is an organic liquid of measurable but limited water miscibility. The term "measurable but limited water miscibility" is defined to mean that the organic liquid must be capable of taking up from about 200 ppm to about 20% by weight of water. This water uptake is based on a two component solvent-water system. We have noted that when carboxylic acid is present, it can have the effect of raising the amount of water which can be taken up by the organic solvent, often by a factor of 2 to 4. A solvent having this property is also referred to herein as a "water-wettable solvent." If the dewatering is carried out by evaporation, the solvent should boil at above $100°$ C. A characteristic of preferred solvents is that they have Lewis base character. This can also be expressed by saying they are polar and electron-donating. One problem with this definition, however, is that certain phosphorylated organic solvents meet this definition but do not give the effect required by the present invention.

The organic solvent can be a single material or it can be a mixture of materials. Ketones having 4 to 8 carbons, for example methyl isobutyl ketone, methyl n-butyl ketone, methyl pentyl ketone, diethyl ketone and the like, can be used as extracting solvents. Cyclic ketones have given very good results. These contain from 5 to about 10 carbon atoms with 5 or 6 carbons making up a 5- or 6-membered aliphatic ring and the remainder being alkyl substituents off the ring. Cyclopentanone, cyclohexanone, methyl cyclohexanone, dimethyl cyclohexanone, and diethyl cyclohexanone are examples of the materials. Six to 10 carbon alcohols such as n-hexanol, cyclohexanol, heptanol, n-octanol, 2-ethyl hexanol, nonanol, and the like can be used. Four- to 8-carbon ethers such as diethyl ether, methyl butyl ether, methyl pentyl ether, and ethyl butyl ether can also be used. Five- to 8-carbon esters such as butyl acetate, pentyl acetate, and the like can be used as well.

The solvent can also contain up to 60% by weight of an amine or the like extractant to enhance the uptake of acid. Typical amines known to be useful in solvent extraction systems include tertiary alkyl amines having in total from about 20 to about 36 carbons in their three alkyl groups. Such materials include trioctyl/decyl amine (Alamine 336, Henkel Corp.), Adogen 363 (Rohm & Haas Corp.) and similar amines marketed by Hoechst.

Preferred solvents are cyclohexanone, methyl cyclohexanone, methyl isobutyl ketone, and methyl n-butyl ketone, alone or together with up to about 60% by wt of an amine, and methyl butyl ether.

The invention will be further described by the following examples.

EXAMPLE 1

An experiment was conducted to demonstrate the key features of the process of the invention. An aqueous solution of fumaric acid was extracted with methyl isobutyl ketone (MIBK). The extract contained 0.0874 moles/liter of acid and 2.1% by weight of water. This extract was then stripped, first to an overhead fraction of 14.19% and subsequently to an overhead fraction of 26.56%. The concentration of water in the bottoms dropped to 0.95% and 0.76% respectively. The amount of the fumaric acid in the methylisobutyl ketone dropped as the water was removed (to 0.0576 moles/liter at 0.95% $H_2O$, and 0.0482 moles/liter at 0.76% $H_2O$) and the excess acid (39.1% and 46.8% respectively) was recovered as a solid precipitate. In a series of supporting experiments, it was shown that if the water was very completely removed to 0.07% by weight, the solubility of the acid in the ketone dropped to 0.0158 moles/liter or less than 1/5th the level observed when a saturation level of water was present.

EXAMPLES 2-3

The feasibility of using the process on aqueous solutions of succinic acid and adipic acid as feed stream was studied. The solubility of these acids was determined in wet and dry MIBK.

|  | Solubility in MIBK | |
| --- | --- | --- |
|  | Acid Conc. moles/liter | Water Conc. moles/liter |
| Succinic Acid | 0.150 | sat'd 0.844 |
|  | 0.030 | dry ~0.15 |
| Adipic Acid | 0.166 | sat'd 0.737 |
|  | 0.048 | dry ~0.15 |

Thus, again it can be seen that reducing the water level of the organic solvent causes acids to precipitate and be recoverable.

EXAMPLE 4

The use of MIBK plus 0.064 M tri-octyl/decyl amine as an organic phase was studied. Again, solubility data showed that the removal of water had a marked effect on the solubility of the acid.

| Acid - Fumaric Acid | |
| --- | --- |
| Acid Concentration moles/liter | Water Concentration moles/liter |
| 0.158 | saturated |
| 0.115 | nearly anhydrous |

EXAMPLE 5

The experiment of Example 4 was repeated using octanol as organic solvent.

| Acid Concentration moles/liter | Water Concentration moles/liter |
| --- | --- |
| 0.0961 | 2.24 |
| 0.0899 | 1.54 |
| 0.0614 | 0.066 |

EXAMPLE 6

The experiment of Example 4 was repeated using butyl ether as organic solvent.

| Acid Concentration moles/liter | Water Concentration moles/liter |
| --- | --- |
| 0.0036 | 0.084 |
| 0.0023 | 0.0005 |

EXAMPLE 7

The experiment of Example 4 was repeated using cyclohexanone as extractant. This showed that this cyclic ketone gave excellent results.

| Acid Concentration moles/liter | Water Concentration g $H_2O$/g solvent |
| --- | --- |
| 0.483 | 0.1 |
| 0.2626 | 0.03 |

| Acid Concentration moles/liter | Water Concentration g $H_2O$/g solvent |
| --- | --- |
| 0.0528 | 0. |

EXAMPLE 8

The experiment of Example 7 was repeated using succinic acid as the acid.

| Acid Concentration moles/liter | Water Concentration g $H_2O$/g solvent |
| --- | --- |
| 1.126 | 0.166 |
| 0.842 | 0.085 |
| 0.54 | 0.055 |
| 0.44 | 0.032 |
| 0.21 | 0.012 |
| 0.14 | 0.0 |

EXAMPLE 9

The experiment of Example 7 was repeated using adipic acid as the acid.

| Acid Concentration moles/liter | Water Concentration g $H_2O$/g solvent |
| --- | --- |
| 1.018 | 0.169 |
| 0.87 | 0.09 |
| 0.50 | 0.04 |
| 0.34 | 0.02 |
| 0.23 | 0.01 |
| 0.16 | 0.0 |

EXAMPLE 10

The experiment of Example 4 was repeated using methylcyclohexanone as solvent and fumaric acid as acid.

| Acid Concentration moles/liter | Water Concentration g $H_2O$/g solvent |
| --- | --- |
| 0.275 | 0.058 |
| 0.22 | 0.04 |
| 0.138 | 0.02 |
| 0.039 | 0.0 |

EXAMPLE 11

The experiment of Example 10 was repeated using succinic acid as the acid.

| Acid Concentration moles/liter | Water Concentration g $H_2O$/g solvent |
| --- | --- |
| 0.50 | 0.076 |
| 0.37 | 0.044 |
| 0.19 | 0.017 |
| 0.13 | 0.008 |
| 0.08 | 0.0 |

EXAMPLE 12

The experiment of Example 10 was repeated using adipic acid as the acid.

| Acid Concentration moles/liter | Water Concentration g H₂O/g solvent |
|---|---|
| 0.58 | 0.88 |
| 0.43 | 0.44 |
| 0.27 | 0.22 |
| 0.19 | 0.11 |
| 0.15 | 0.006 |
| 0.10 | 0.0 |

COMPARATIVE EXPERIMENTS

To demonstrate the criticality of using an appropriate organic liquid, experiments were run using toluene plus amine and tributyl phosphate as organic phase and fumaric acid as the acid with the following negative results which would not permit the practice of the present invention.

| Acid Conc. moles/liter | Water Conc. moles/liter |
|---|---|
| Toluene plus 0.0612 M amine | |
| 0.46 | 0.55 |
| 0.43 | 0.27 |
| Tributyl Phosphate | |
| 0.76 | 2.75 |
| 0.85 | 0.155 |

We claim:

1. A process for recovering carboxylic acid selected from the group consisting of aliphatic polycarboxylic acids of 2 to 12 carbon atoms, aromatic monocarboxylic acids of 7 to 13 carbon atoms and aromatic polycarboxylic acids of 8 to 12 carbon atoms from a solution in a water-wet polar electron donating non-phosphoryl organic solvent liquid phase comprising
    a) reducing the water content of the liquid phase thereby creating a liquid phase in which the carboxylic acid is less soluble and thereby causing a solid precipitate of the carboxylic acid and
    b) recovering the solid precipitate of the carboxylic acid from the reduced water content liquid phase.

2. The process of claim 1 wherein the step a) the reducing of water is by stripping.

3. The process of claim 2 wherein the stripping is conducted at elevated temperatures.

4. The process of claim 2 wherein the stripping is conducted at reduced pressure.

5. The process of claim 1 wherein the organic solvent comprises a solvent selected from the group consisting of 3 to 8 carbon ketones, 5 to 10 carbon alcohols, 4 to 8 carbon ethers and 4 to 10 carbon esters.

6. The process of claim 1 wherein the carboxylic acid is a polycarboxylic acid.

7. The process of claim 6 wherein the polycarboxylic acid is a dicarboxylic acid.

8. The process of claim 6 wherein the polycarboxylic acid is a tricarboxylic acid.

9. The process of claim 1 wherein the carboxylic acid is selected from the group consisting of benzoic acid, cinnamic acid, phenylacetic acid, naphthoic acid, oxalic acid, succinic acid, adipic acid, suberic acid, sebacic acid, fumaric acid, and phthalic acid.

10. The process of claim 1 wherein the solution additionally comprises a second carboxylic acid selected for the same group said second carboxylic acid being more soluble in the organic solvent phase than the carboxylic acid and from which the acid is preferentially separated.

11. The process of claim 1 wherein the water-wet organic solvent liquid phase is an organic solvent extract of an aqueous solution which contains the carboxylic acid.

12. The process of claim 2 wherein the acid is adipic acid.

13. The process of claim 12 wherein the solvent is cyclohexanone.

14. The process of claim 12 wherein the solvent is methylcyclohexanone.

15. A process for recovering a nonvolatile carboxylic acid selected from the group consisting of aliphatic polycarboxylic acids of 2 to 12 carbon atoms, aromatic monocarboxylic acids of 7 to 13 carbon atoms and aromatic polycarboxylic acids of 8 to 12 carbon atoms from an aqueous starting solution comprising
    a) contacting the aqueous starting solution with a polar electron donating non-phosphoryl organic solvent of measurable but limited water miscibility thereby forming a carboxylic acid depleted aqueous solution phase and a carboxylic acid enriched water wet organic solvent phase,
    b) separating the carboxylic acid depleted aqueous solvent from the carboxylic acid enriched water wet organic solvent phase,
    c) reducing the water content of the organic solvent phase thereby creating a liquid phase in which the carboxylic acid is less soluble and thereby causing a solid precipitate of the carboxylic acid and
    d) recovering the solid precipitate of the carboxylic acid from the liquid phase.

16. The process of claim 15 wherein step c) the reducing of water is by stripping.

17. The process of claim 15 wherein the organic solvent comprises a solvent selected from the group consisting of 3 to 8 carbon ketones, 5 to 10 carbon alcohols, 4 to 8 carbon ethers and 4 to 10 carbon esters.

18. The process of claim 15 wherein the carboxylic acid is selected from the group consisting of benzoic acid, cinnamic acid, phenylacetic acid, naphthoic acid, oxalic acid, succinic acid, adipic acid, suberic acid, sebacic acid, fumaric acid, and phthalic acid.

19. The process of claim 18 wherein the acid is adipic acid.

20. The process of claim 19 wherein the solvent is cyclohexanone.

21. The process of claim 19 wherein the solvent is methylcyclohexanone.

22. A process for recovering a carboxylic acid selected from the group consisting of aliphatic polycarboxylic acids of 2 to 12 carbon atoms, aromatic monocarboxylic acids of 7 to 12 carbon atoms and aromatic polycarboxylic acids of 8 to 12 carbon atoms from an aqueous starting solution comprising
    a) contacting the aqueous starting solution with a polar electron-donating non-phosphoryl organic solvent of measurable but limited water miscibility thereby forming a carboxylic acid depleted aqueous solution phase and a carboxylic acid enriched water wet organic solvent phase,
    b) separating the carboxylic acid depleted aqueous solution from the carboxylic acid enriched water wet organic solvent phase,
    c) stripping the carboxylic acid enriched water wet organic solvent phase to take off water and organic solvent as an overhead stream, and generating a carboxylic acid containing solvent bottoms product.

d) precipitating the carboxylic acid as a solid from the bottoms product and e) recovering the solid carboxylic acid so formed.

23. The process of claim 22 wherein a mother liquor resulting from the precipitating of step d) is recovered and returned to the contacting of step a).

24. The process of claim 22 wherein the water and organic solvent containing overhead stream of step c) is recovered, split into a water phase and an organic solvent phase, and the organic solvent phase is returned to the contacting of step a).

25. The process of claim 24 wherein the carboxylic acid is selected from the group consisting of benzoic acid, cinnamic acid, phenylacetic acid, naphthoic acid, oxalic acid, succinic acid, adipic acid, suberic acid, sebacic acid, fumaric acid, and phthalic acid.

26. The process of claim 24 wherein the organic solvent comprises a solvent selected from the group consisting of 3 to 8 carbon ketones, 5 to 10 carbon alcohols, 4 to 8 carbon ethers and 4 to 10 carbon esters.

27. The process of claim 24 wherein the acid is adipic acid.

28. The process of claim 24 wherein the solvent is cyclohexanone.

29. The process of claim 24 wherein the solvent is methylcyclohexanone.

* * * * *